US009042992B2

(12) United States Patent
Dixon et al.

(10) Patent No.: US 9,042,992 B2
(45) Date of Patent: May 26, 2015

(54) PROTECTING AIRWAYS

(71) Applicant: University of Florida Research Foundation, Inc, Gainesville, FL (US)

(72) Inventors: Warren E. Dixon, Gainesville, FL (US); Donald Clementz Bolser, Gainesville, FL (US); Teresa Elizabeth Pitts, Gainesville, FL (US); Sean Conrad McCoy, Gainesville, FL (US)

(73) Assignees: University of Florida Research Foundation, Inc., Gainesville, FL (US); The United States of America as represented by the Department of Veteran's Affairs, Washington, DC (US)

( * ) Notice: Subject to any disclaimer, the term of this patent is extended or adjusted under 35 U.S.C. 154(b) by 0 days.

(21) Appl. No.: 14/014,835

(22) Filed: Aug. 30, 2013

(65) Prior Publication Data
US 2014/0067008 A1 Mar. 6, 2014

Related U.S. Application Data

(60) Provisional application No. 61/695,515, filed on Aug. 31, 2012.

(51) Int. Cl.
*A61N 1/00* (2006.01)
*A61N 1/36* (2006.01)
(52) U.S. Cl.
CPC .......... *A61N 1/36003* (2013.01); *A61N 1/3601* (2013.01); *A61N 1/36014* (2013.01); *A61N 1/36017* (2013.01)
(58) Field of Classification Search
CPC ....................................................... A61N 1/18
USPC ....................................................... 607/2, 48
See application file for complete search history.

(56) References Cited

U.S. PATENT DOCUMENTS 5,397,337 A * 3/1995 Jaeger et al. .................... 607/62
5,891,185 A 4/1999 Freed et al.
(Continued)

FOREIGN PATENT DOCUMENTS

EP 2108313 10/2009
WO 0195666 12/2001
(Continued)

OTHER PUBLICATIONS

Cabre, M., Serra-Prat, M., Palomera, E., Almirall, J., Pallares, R., & Clave, P. (2010). Prevalence and prognostic implications of dysphagia in elderly patients with pneumonia. Age and ageing, 39(1), 39.
(Continued)

*Primary Examiner* — Christopher D Koharski
*Assistant Examiner* — Nadia A Mahmood
(74) *Attorney, Agent, or Firm* — Fleit Gibbons Gutman Bongini & Bianco PL; Paul D. Bianco; Gary S. Winer

(57) ABSTRACT

An airway of a patient is protected from intrusion of contaminants by monitoring muscles of the patient to detect an attempted cough or swallow, and applying an electrical stimulus to the neck of the patient, varying amplitude and/or frequency over time, the applied electrical stimulus operates to promote an efficacious cough or swallow. The electrical stimulus induces a voltage within a range of greater than zero volts and less than 20 volts, and the frequency have patterned changes between at least about 4 Hz to not more than about 30 Hz. The monitoring is carried out by an electronic device, and the patient may indicate to the electronic device that a swallow or cough is impending.

21 Claims, 8 Drawing Sheets

(56) References Cited

U.S. PATENT DOCUMENTS

| | | | |
|---|---|---|---|
| 7,292,890 B2 * | 11/2007 | Whitehurst et al. | 607/45 |
| 7,672,728 B2 | 3/2010 | Libbus et al. | |
| 7,769,461 B2 | 8/2010 | Whitehurst et al. | |
| 7,797,050 B2 | 9/2010 | Libbus et al. | |
| 8,092,433 B2 | 1/2012 | Hamdy | |
| 8,114,030 B2 | 2/2012 | Ales et al. | |
| 8,211,040 B2 | 7/2012 | Kojima et al. | |
| 8,372,020 B2 | 2/2013 | Martin et al. | |
| 2002/0133194 A1 | 9/2002 | Leelamanit | |
| 2003/0093128 A1 | 5/2003 | Freed et al. | |
| 2005/0126578 A1 | 6/2005 | Garrison et al. | |
| 2006/0064037 A1 | 3/2006 | Shalon et al. | |
| 2007/0123950 A1 | 5/2007 | Ludlow | |
| 2007/0150006 A1 | 6/2007 | Libbus | |
| 2008/0234781 A1 | 9/2008 | Einav et al. | |
| 2009/0054980 A1 | 2/2009 | Ludlow | |
| 2010/0125310 A1 | 5/2010 | Wilson | |
| 2011/0009920 A1 | 1/2011 | Whitehurst | |
| 2011/0093032 A1 | 4/2011 | Boggs, II | |
| 2011/0202106 A1 | 8/2011 | Bolea et al. | |
| 2012/0111329 A1 | 5/2012 | Brand et al. | |
| 2012/0253249 A1 | 10/2012 | Wilson | |
| 2013/0079634 A1 | 3/2013 | Kerber | |

FOREIGN PATENT DOCUMENTS

| | | |
|---|---|---|
| WO | 2005062829 | 7/2005 |
| WO | 2008048471 | 4/2008 |
| WO | 2010057286 | 5/2010 |
| WO | 2011008749 | 1/2011 |
| WO | 2011016864 | 10/2011 |
| WO | 2012134505 | 10/2012 |
| WO | 2014036425 | 3/2014 |

OTHER PUBLICATIONS

Smith Hammond, C. A., Goldstein, L. B., Zajac, D. J., Gray, L., Davenport, P. W., & Bolser, D. C. (2001). Assessment of aspiration risk in stroke patients with quantiication of voluntary cough. Neurology, 56(4), 502-506.

Sue Eisenstadt, E. (2010). Dysphagia and aspiration pneumonia in older adults. Journal of the American academy of Nurse Practitioners, 22(1), 17-22.

Van Den Eeden, S.K., et al., Incidence of Parkinson's disease: variation by age, gender, and race/ethnicity. American Journal of Epidemiology, 2003. 157(11): p. 1015-1022.

Brookmeyer, R., S. Gray, and C. Kawas, Projections of Alzheimer's disease in the United States and the public health impact of delaying disease onset. American Journal of Public Health, 1998. 88(9): p. 1337.

Fernandez, H. and K. Lapane, Predictors of mortality among nursing home residents with a diagnosis of Parkinson's disease. Medical science monitor: international medical journal of experimental and clinical research, 2002. 8(4).

Ertekin, C. and J.B. Palmer, Physiology and electromyography of swallowing and its disorders. Suppl Clin Neurophysiol, 2000. 53: p. 148-54.

Jean, A., Brain stem control of swallowing: neuronal network and cellular mechanisms. Physiological Review, 2001. 81(2): p. 929-69.

Canning, B.J., Anatomy and neurophysiology of the cough reflex. Chest, 2006. 129(1 suppl): p. 33S.

Satoh, I., et al., Upper airway motor outputs during sneezing and coughing in decerebrate cats. Neuroscience research, 1998. 32(2): p. 131-135.

Gestreau, C., et al., Activity of dorsal respiratory group inspiratory neurons during laryngeal-induced fictive coughing and swallowing in decerebrate cats. Experimental brain research, 1996. 108(2): p. 247-256.

Lalmohamed A, et al., Causes of death in patients with multiple sclerosis and matched referent subjects: a population-based cohort study. Eur J Neurol., 2012.

Lechtzin N., Respiratory effects of amyotrophic lateral sclerosis: problems and solutions. Respir Care, 2006. 51(8) 871-81.

www.vitalstim.com—VitalStim Therapy—A breakthrough therapy for the treatment of dysphagia, dated Aug. 27, 2012.

Wikipedia encyclopedia—Afferent nerve fiber—pp. 2, retrieved Mar. 12, 2014.

Wikipedia encyclopedia—Efferent nerve fiber—pp. 2, retrieved Mar. 12, 2014.

ISR Search Report for PCT/US13/57564, dated Nov. 16, 2013.

* cited by examiner

PROTECTING AIRWAYS

FIELD OF THE INVENTION

The invention relates to a system and method for protecting the airway, and in particular, promoting an efficacious cough and swallow.

BACKGROUND OF THE INVENTION

A variety of neuromuscular diseases result in dystussia and/or dysphagia (disordered swallow). Recent research in clinical populations has documented that many of these patients have a disorder of airway protection consisting of both dystussia and dysphagia, including amyotrophic lateral sclerosis (ALS), multiple sclerosis, stroke and Parkinson's disease (PD) (Cabre et al., 2010; Jones, Enright, & Busse, 2011; Sue Eisenstadt, 2010; Lechtzin et al., 2006; Lalmohamed A et al., 2012). Voluntary and reflexive cough have been shown to detect and/or predict dysphagia in stroke and Parkinson's disease (Pitts et al., 2010; Smith Hammond et al., 2009; Smith Hammond et al., 2001), and in Parkinson's disease and Alzheimer's disease the leading cause of death is aspiration pneumonia.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 CFR §1.56(a) exists.

SUMMARY OF THE INVENTION

In accordance with the disclosure, a method of improving airway protection in patient populations comprises of 1) monitoring muscle activity to detect a cough and/or swallow, 2) applying an electrical stimulus to the neck of the patient, and 3) varying the amplitude and/or frequency of the stimulus to enhance or promote an efficacious cough and/or swallow.

In embodiments thereof, the electrical stimulus including a voltage within a range of greater than zero volts and less than 20 volts; the frequency is varied, and wherein the frequency is swept within a range of greater than 1 Hz and less than 30 Hz; an electrical stimulus is applied before the patient has attempted to swallow, and an electrical stimulus is applied between about 1 millisecond to about 0.5 seconds after the patient has attempted to swallow or has swallowed; the electrical stimulus is applied after a substantial increase in a set of muscles stereotypical electromyographic (EMG) activity. It should be understood, however, that patients who present greater barriers to transmission of an electrical signal into the body, for example patients with relatively large amount of adipose tissue, or high skin thickness, may require higher voltages, as determined by the medical practitioner, weighing the patient's individual tolerances and safety.

In further embodiments thereof, monitoring muscles is performed using EMG; sensed EMG information is analyzed by one or more computer processors, the processors operative to initiate the program to alter the electrical stimulus during the execution of the behavior response; monitoring of muscles of the patient is carried out by an electronic device; and the patient may also indicate to the electronic device that a swallow or cough is impending. Further, a computer processor is advantageously used to analyze and "model" or "fit" a particular patient's muscular responses of the disorder cough or swallow, and apply an appropriate voltage and frequency pattern to modulate or normalize the cough or swallow. In one embodiment, the computer processor executes software capable of learning, using, for example, a neural network algorithm.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

In accordance with the disclosure, the airway is protected to improve a state of health of patients, and in the case of certain diseases such as Multiple Sclerosis (MS), Amyotrophic Lateral Sclerosis (ALS), ischemic or hemorrhagic stroke, Parkinson's (PD) and Alzheimer's (AD), to reduce an incidence of aspiration pneumonia and subsequent death resulting from impaired airway protection. Further, the disclosure provides for observing and controlling both cough and swallow in order to ameliorate airway protective disorders, for example in patients with neurodegenerative diseases. For example, PD and AD together affect approximately 6 million people in the United States, and dysphagia and dystussia are primary factors in the death of PD and AD patients. In addition, stroke will affect nearly 1 million people per year in the United States at a cost of 73.7 billion USD for related medical costs and disability (per www.strokeassociation.org, accessed Jul. 15, 2012). MS and ALS affect nearly 0.5 million people in the U.S., however the average life expectancy following ALS diagnosis is approximately 3 years.

Figure 1:
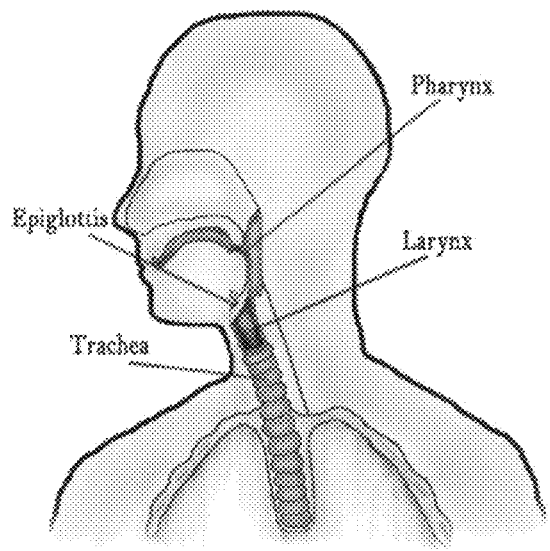
FIG. 1 depicts a prior art diagram of the airway and associated physiological structures of a patient.
Figure 2A:
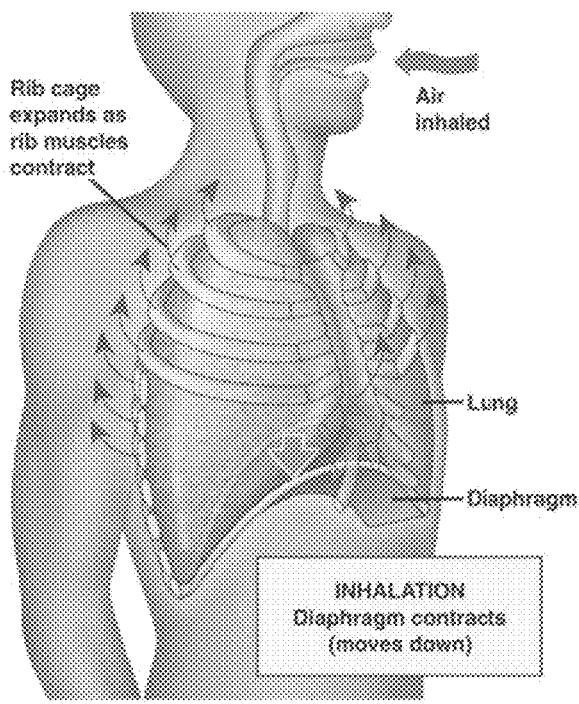
FIG. 2A depicts a prior art diagram of inhalation by the patient.
Figure 2B:
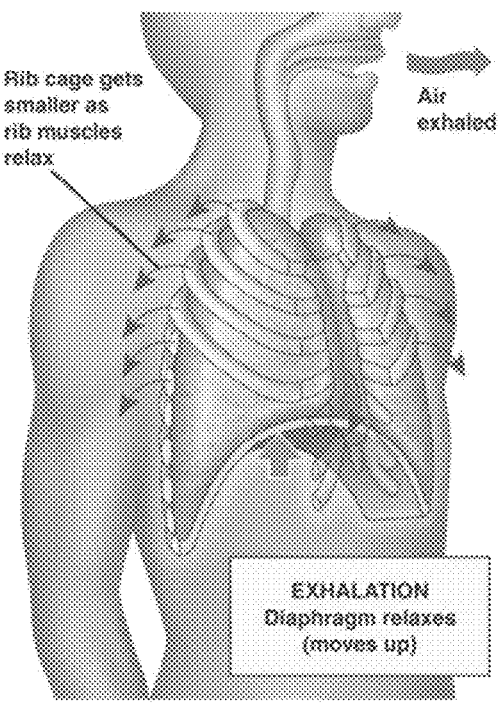
FIG. 2B depicts a prior art diagram of exhalation by the patient.
Figure 3:
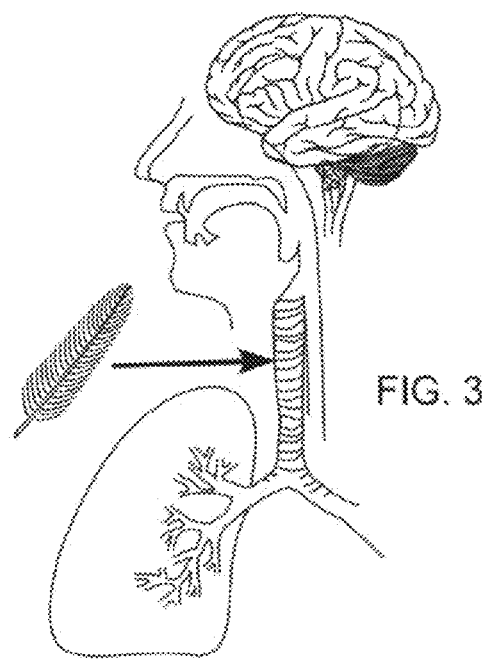
FIG. 3 depicts mechanical stimulation of the trachea to produce a cough or swallow.

With reference to FIGS. 1 and 2A-2B, an overview of certain aspects of the behavior of the respiratory system may be understood, including two phases of breathing. In FIG. 2A, inhalation is illustrated, in which the diaphragm and intercostals muscles contract, and the diaphragm moves down, increasing lung volume. In FIG. 2B, exhalation is illustrated, in which the inspiratory muscles relax, the diaphragm moves up, and lung volume decreases.

Swallowing is a complex coordinated behavior, in which the body normally protects the airway by sealing the trachea to prevent aspiration, or entry of material, into the airway. Dysphagia is a swallowing disorder manifesting an uncoordinated swallowing behavior. Swallowing may be induced by sensory feedback from the tongue, uvula, epiglottis, pharynx, esophagus, or other points of the body. Without being bound to a particular theory, it is considered herein that swallowing mechanisms are coordinated or controlled, at least in part, by a network of neurons within the brainstem, termed behavior control assemblies (BCA's).

Coughing is a defensive reflex triggered, for example, by aspiration. There are typically three phases: (1) inhalation, (2) vocal fold adduction in which the trachea is sealed and pressure is built up in the lungs by contraction of abdominal muscles, and (3) ballistic expiration including a rapid opening of the trachea and an explosive release of air generating high linear airflow velocities and shearing forces that remove material from the airway. Dystussia refers to a coughing disorder, usually resulting in decreased cough strength, or increased compression phase duration (transition time from the inspiratory to expiratory phase). Similarly with respect to swallowing, without being bound to a particular theory, it is considered herein that coughing is also controlled, at least in part, by BCAs. Accordingly, in one embodiment of the disclosure, the brain, and particularly BCAs, are stimulated or influenced by an electrical signal from a device 300 of the disclosure.

Figure 7:
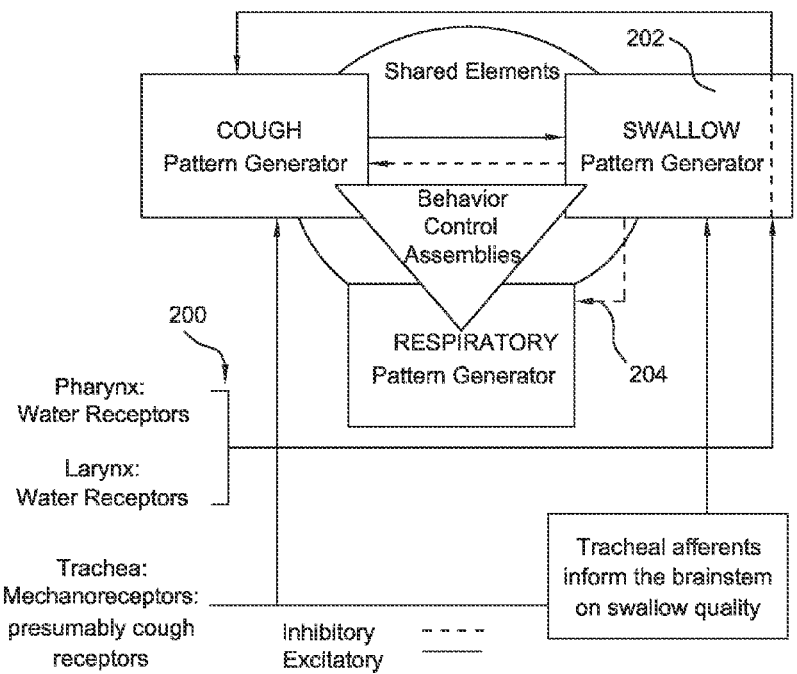
FIG. 7 illustrates inhibitory and excitatory pathways in the patient, and behavior controls, within the patient.

With reference to FIG. 7, an actual or conceptual control pathway is illustrated, the pathway advantageously utilized to carry out the disclosure. In particular, water or liquid receptors in the pharynx and or larynx (200), including areas in the back of the throat or proximate the back of the throat or mouth, trigger swallowing (202), possibly to move material away from the trachea. Accordingly, a disordered swallow, or a simulated disordered swallow, may be used to trigger such response. The triggered swallowing in turn triggers a response in the respiratory system (204) to pause breathing and to seal the trachea (inhibitory), or alternatively to initiate a cough in the event that material has entered the trachea or lungs. In accordance with the disclosure, both excitatory and inhibitory pathways are formed between the swallow pattern generator and the cough pattern generator, wherein a disordered swallow triggers a cough, for example.

In accordance with one embodiment of the disclosure, the patient may initiate a programmed change in the electrical stimulation (for example by pressing a button to produce an efficacious cough and/or swallow. Alternatively, EMG activity is tracked by a device of the disclosure, and a programmed change in the electrical stimulation is initiated independent of the patient as described herein. In another embodiment, the patient can indicate to the device that a swallow and or cough is expected, for example prior to eating or drinking, to "pre-sensitize" the device, or alter device parameters to increase a likelihood of electrical stimulation. Such indication may take place in the form of a switch setting on the device, a gesture carried out upon the device, or by the individual, or a spoken command understood by the device.

The device and methods of the disclosure work to improve airway protection in the manner described herein, regardless of an identification of correct physiological theories. However, it is advantageous to consider, in understanding the disclosure, that it is possible for afferent nerves leading from the throat, trachea, mouth, and or esophagus to communicate information pertaining to the quality of the swallow to the brain, and possibly the BCA area of the brain, which may operate to then trigger coordinated cough and swallow patterns, in coordination with respiratory patterns. In one embodiment, the swallow pattern is coordinated with the cough pattern, to move expelled or invading material into the esophagus, away from the trachea.

Figure 18:
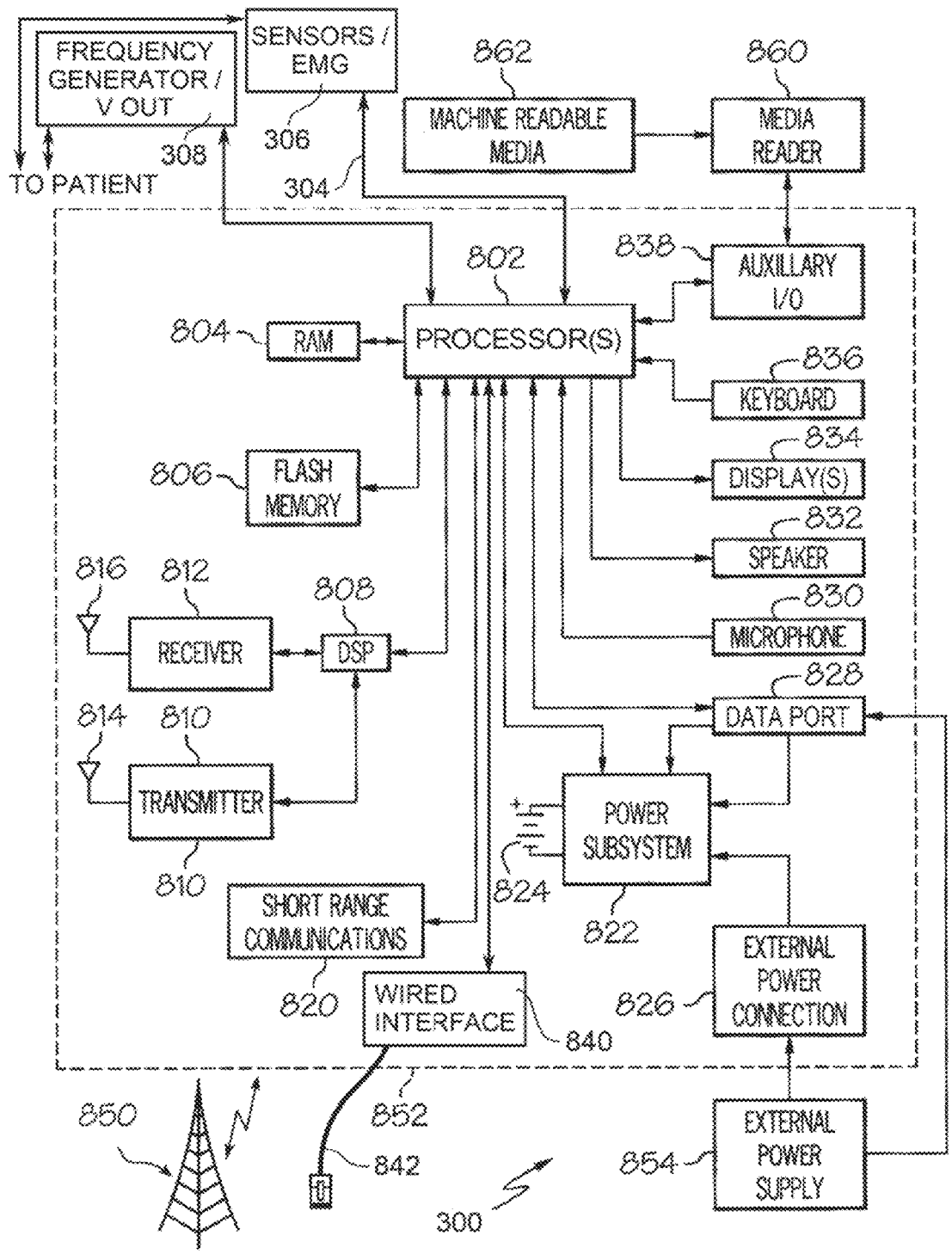
FIG. 18 is a block diagram of components that may be associated with a device of the disclosure.

Thus, in accordance with the disclosure, the trachea is mechanically stimulated (FIG. 18, 310) to stimulate a cough, and in one embodiment, a repetitive cough. Additionally or alternatively, a liquid, such as water, is admitted into the pharynx, for example by injection, triggering a swallow. For testing, injection of fluids may be carried out by a mechanical or robotic fluid introducer device 310 (FIG. 18), including a fluid supply and an applicator, and a hose if the fluid supply is remote from the applicator (not shown). In accordance with the disclosure, an electrical stimulation, advantageously of the superior laryngeal nerve (SLN), promotes either a swallow, cough, or both, advantageously dependent upon stimulation parameters. The electrical stimulation may be provided by a signal generator, for example a frequency generator, and power supply (V out) 308 under control of a processor 802 (FIG. 18). Power for generator/supply 308 may be provided by an onboard battery of a device, or an external power supply. Any or all of these events is advantageously triggered by EMG measurements carried out by sensors and or an EMG device or subunit (FIG. 18, 306), and or esophageal pressure, also measured by sensors 306.

In accordance with the disclosure, a customized or patient specific algorithm will be determined and implemented, based upon successful swallow data. The customized algorithm can be remotely modified by a clinician or other medical practitioner, or may be modified at a clinic, to adapt parameters of the algorithm to the patient's changing medical condition, for example in response to a cold infection, disease progression, further brain injury, or other physiological change.

Figure 4:
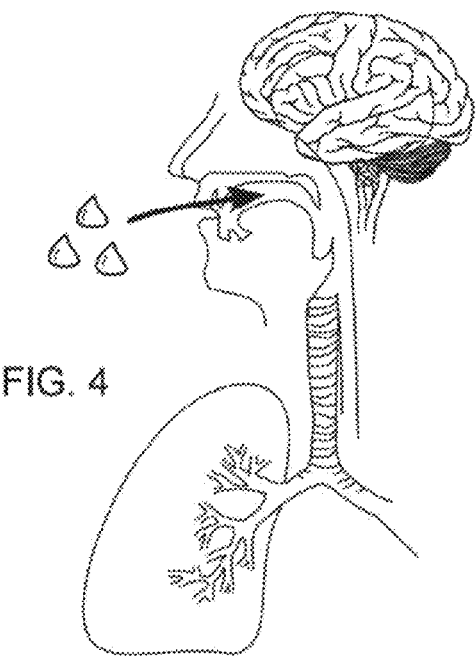
FIG. 4 depicts stimulation of the trachea by introduction of fluids into the mouth of the patient to produce a cough or swallow.
Figure 5:
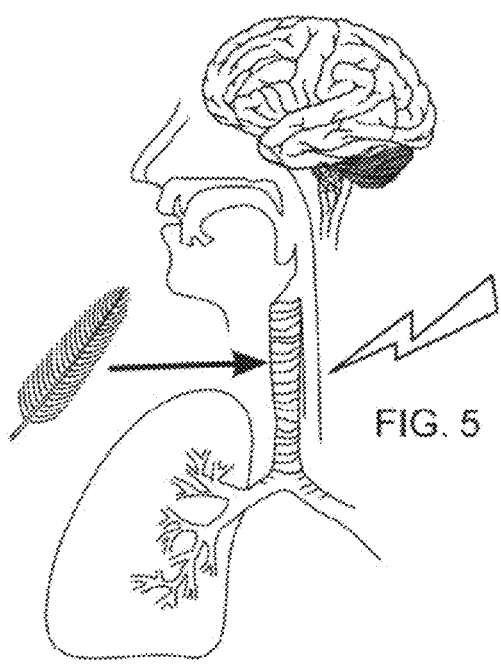
FIG. 5 depicts mechanical stimulation of the trachea to produce a cough or swallow, accompanied by an electrical signal of the disclosure to produce an efficacious cough or swallow.
Figure 6:
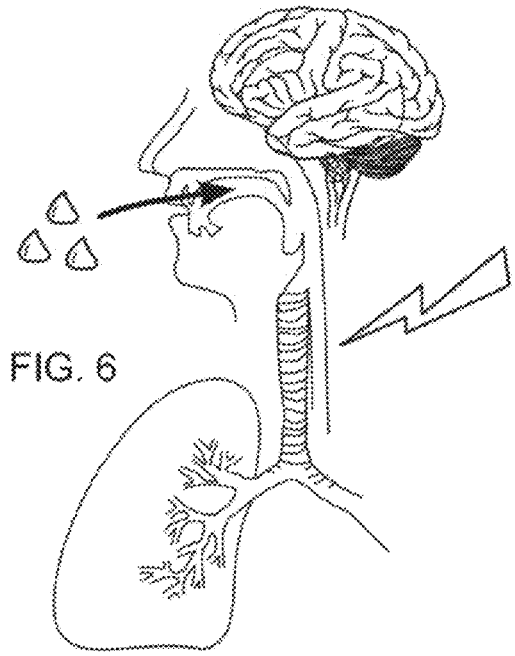
FIG. 6 depicts stimulation of the trachea by introduction of fluids into the mouth of the patient to produce a cough or swallow, accompanied by an electrical signal of the disclosure to produce an efficacious cough or swallow.

Referring now to FIGS. 3-8, it may be seen that the trachea is mechanically stimulated for testing. In the illustration, a feather is illustrated, however it should be understood that mechanical stimulation of the trachea may be carried out by any object, for example by introduction of a thin polymeric cannula. For example, a robotic or mechanical stimulator 312 may be positioned proximate the trachea, inside or outside of the body, under control of processor 802 (FIG. 18). A feather is illustrated because a light and varying mechanical pressure, as in tickling, is advantageous. In FIG. 4, introduction of a liquid to the mouth is carried out, which herein includes the pharynx or back of the mouth. The liquid introduced by any known or hereinafter developed means, including for example a dropper, syringe, or spray nozzle. Introduction of fluid may be carried out, in one embodiment, in response to a detected effort to cough or swallow by the patient. FIGS. 5-6 symbolically indicate the additional use of electrical stimulation, as described herein, in addition to the stimuli described for FIGS. 3 and 4, respectively. The application of an electrical, and EMG measurements, are all advantageously carried out non-invasively, and more particularly, without forming an opening in the patient's body. Similarly, electrical stimulation may be carried out in response to an attempt to cough or swallow by the patient.

In one embodiment, a device of the disclosure is triggered by behavior-specific markers in EMG, to provide behavior-specific programmed surface electrical stimulation routines to shape cough and swallow production. An electrical signal is delivered by a plurality of electrodes, and in one embodiment a pair of electrodes, placed in accordance with one embodiment, lateral to the larynx, one electrode placed superior to the thyroid cartilage, and the other electrode placed inferior to the cricoid cartilage. However, it should be understood that other placements may be used.

In one embodiment, the voltage and frequency delivered by the electrodes is varied during application. To modify a series of repetitive coughs, for example, a slow waveform is applied, for example a patterned frequency change between 4 to 20 Hz, with an upward ramping of voltage from >0 to 7 volts, is carried out over a period of about 5 to about 20 seconds. In one embodiment, the voltage is as high as 20 volts, and the period as long as 60 seconds. Further, these periods of stimulation may be repeated up to every few minutes for time spans of 24 hours to weeks. It should be understood that the signal generator/power supply 308 may be used to adjust pulse width, frequency, and or amplitude to alter the stimulation for optimal results for a patient. Examples of a patterned frequency change include triangular, sweep, stepped, fixed, various, sinusoid, spike, square, monophasic, and biphasic. In one embodiment, varying the frequency is employed to advantageously decrease a possibility of habituation to the stimulus by the patient. In another embodiment, the signal may be applied for periods longer than 20 seconds, to bring about synaptic plasticity, for example synaptic improvements associated with swallowing, to improve independent functionality of the patient.

This stimulus is advantageously triggered by an increase in esophageal pressure, to improve the force and efficacy of a cough. Additionally or alternatively, a patterned frequency change between 4 to 20 Hz is carried out at a constant 5 volts until, for example, about 0.25 to 0.75 seconds after a swallow has occurred. Higher frequencies have also found to be effective, for example about 30 Hz. In accordance with the disclosure, the stimulus develops normal swallows, which are advantageously swallows that move food material at normal speed through the pharynx and are without penetration or aspiration into the vocal folds or trachea. This stimulus is advantageously triggered by an EMG signal indicative of an attempted swallow, and promotes a timely and effective swallow. These frequencies, voltages, and timing are illustrative only, and represent one pattern that has been found to be advantageous for the recited purpose. It should be understood, that significant variations are contemplated. It should further be understood that effective voltages ranges may vary proportionate to the size of the neck, an amount of submental fat, and a thickness of the skin. More particularly, in accordance with the disclosure, it has been found that a novel program of varying frequency and varying voltage (amplitude and or pulse width), generally, can modify the production of a cough, and that a varying frequency and constant voltage, generally, can modify the production of a swallow, and that application of these electrical stimuli are best carried out in response to the body's attempt to initiate a cough or swallow, respectively. These two application modes are embodied within the device to initiate the desired behavior from the patient. Without being bound by a particular theory, it is possible that application of voltage in the manner described above causes a signal to be transmitted along tracheal and esophageal afferent nerves, to the brainstem, thereby modifying the physiological response, and in particular, shaping the production of a cough and or a swallow.

In one embodiment, application of voltage to the patient is in response to an attempt to cough or swallow, as detected by sensors connected to muscles of the patient, advantageously as interpreted by one or more processors. In another embodiment, application of voltage is coordinated with either or both of introduction of fluids to the mouth, or mechanical stimulation of the trachea or other tissue of the neck area, in order to stimulate or promote an efficacious cough or swallow, thereby protecting the airway from the introduction of unwanted material.

Figure 8:
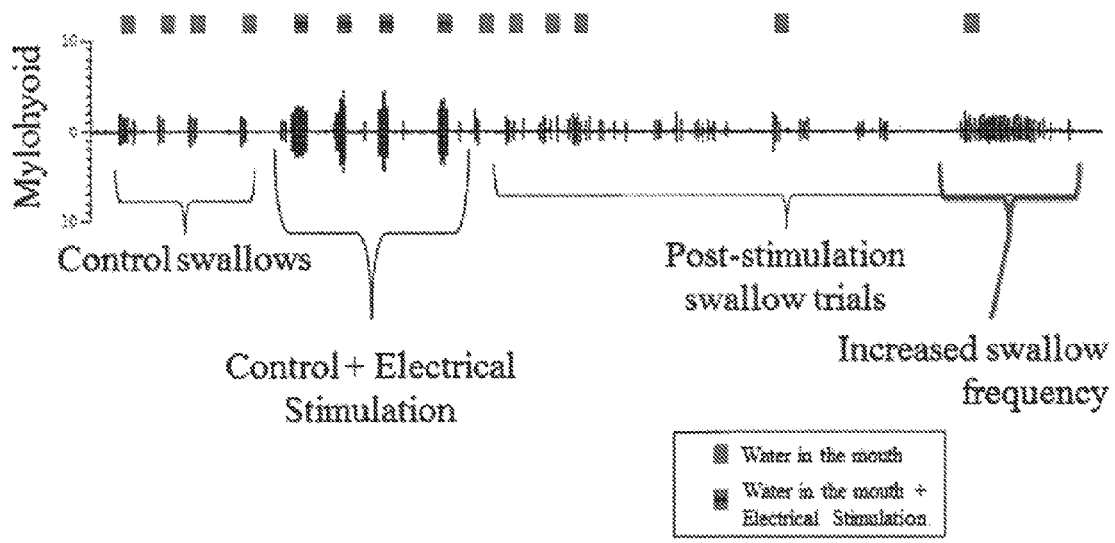
FIG. 8 is a graph of electrical activity of the mylohyoid muscle in with and without electrical stimulation in accordance with the disclosure.

Referring now to FIG. 8, the stimuli of water in the mouth, or a combination of water in the mouth plus electrical stimulation, as described herein, accompanies an attempt to swallow. The graph indicates electrical activity of the mylohyoid muscle (located under the chin) as a marker, or indication of the incidence and force of a swallow. It may be seen that the electrical stimulation as described herein, significantly increases the force of a swallow. It may additionally be seen that surface electrical stimulation increased the excitability of swallow from an injection of water in the mouth during post-stimulation swallowing. In accordance with the disclosure, in patients with impaired swallow, the activity of the muscles generating a swallow is ballistic-like, or spasmotic. However, their duration of activity is very short, on the order of 200 milliseconds, typically.

Figure 9:
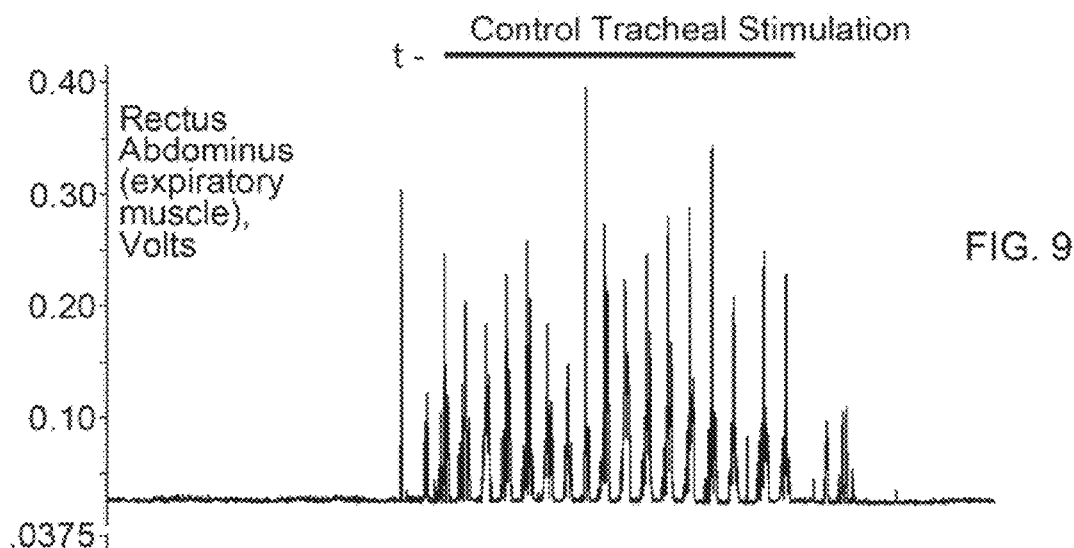
FIG. 9 illustrates a control in which mechanical stimulation is applied to the trachea, and electrical activity of the rectus abdominus muscle is measured.
Figure 10:
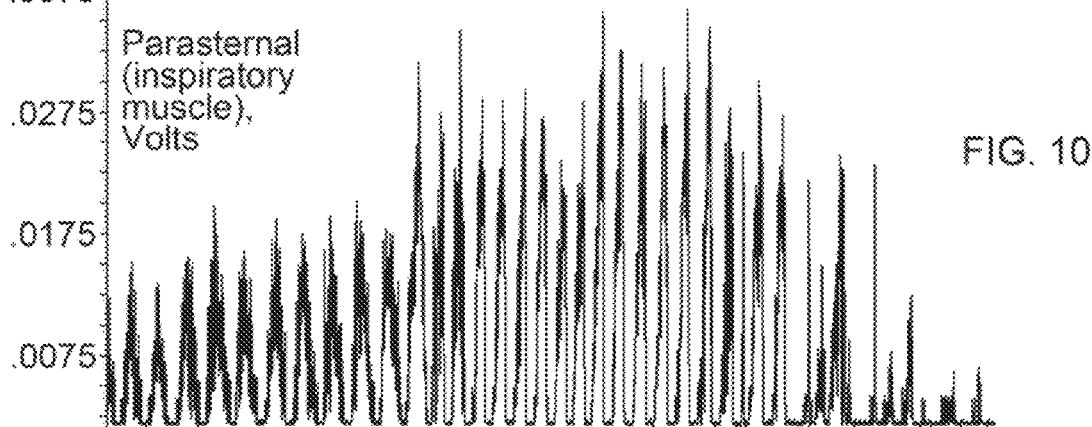
FIG. 10 illustrates a control in which mechanical stimulation is applied to the trachea, and electrical activity of the parasternal muscle is measured.
Figure 11:
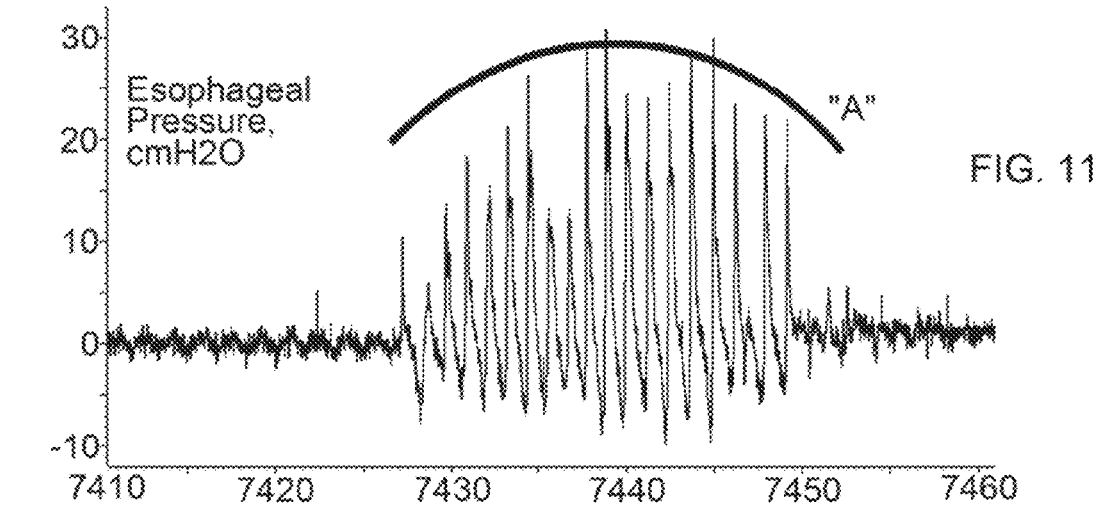
FIG. 11 illustrates a control in which mechanical stimulation is applied to the trachea, and esophageal pressure is measured.
Figure 12:
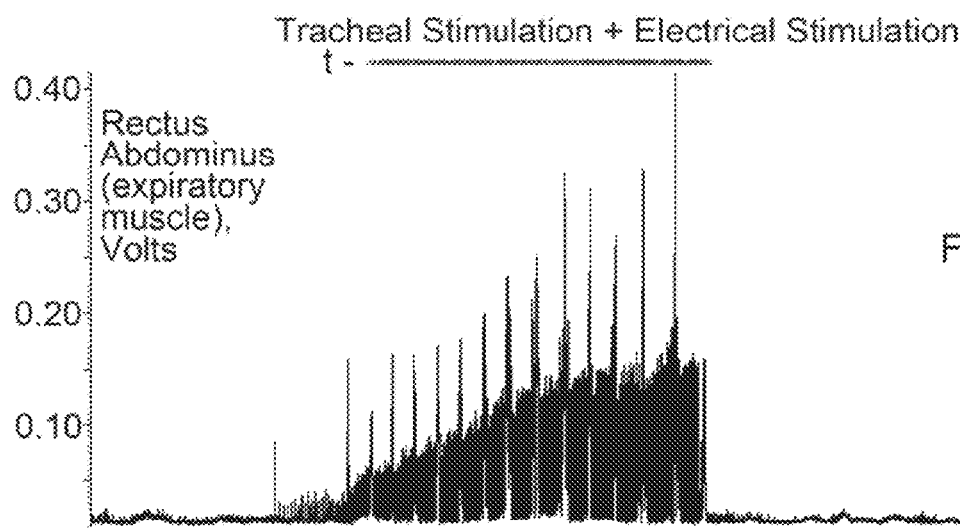
FIG. 12 illustrates a mechanical stimulation applied to the trachea, with electrical stimulation in accordance with the disclosure, wherein electrical activity of the rectus abdominus muscle is measured.
Figure 13:
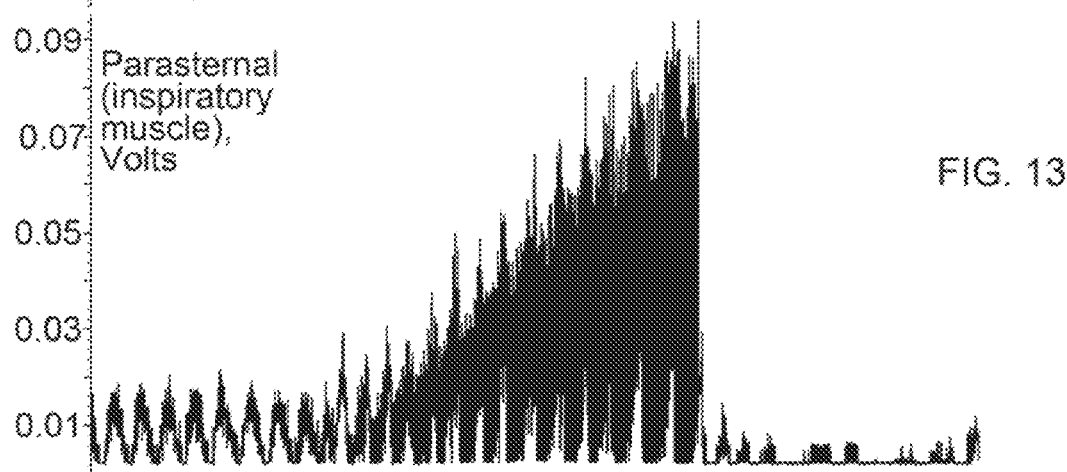
FIG. 13 illustrates a mechanical stimulation applied to the trachea, with electrical stimulation in accordance with the disclosure, wherein electrical activity of the parasternal muscle is measured.
Figure 14:
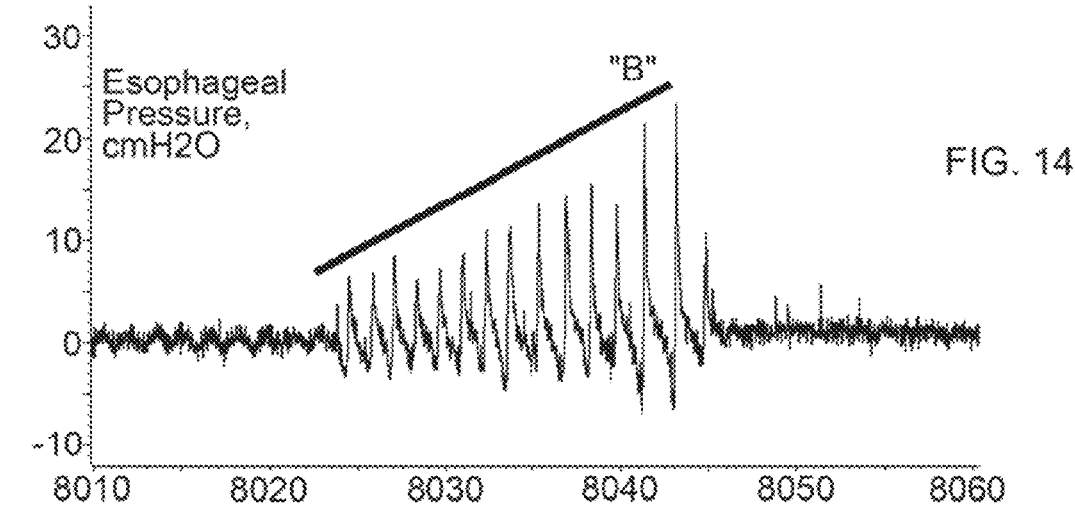
FIG. 14 illustrates a mechanical stimulation applied to the trachea, with electrical stimulation in accordance with the disclosure, wherein esophageal pressure is measured.

In FIGS. 9-14, electrical stimulation to the neck, in which the stimulus was linearly increased over the 20 second period, changed the cough expiratory phase motor drive. In FIGS. 9-11, control mechanical tracheal stimulation is illustrated. It may be seen in FIG. 11 that pressure within the esophagus follows a curved pattern (curve "A"), with pressure gradually increasing, and then gradually decreasing. In FIGS. 12-14, electrical stimulation as described herein is applied, together with tracheal stimulation, producing a ramped increase (line "B") in esophageal pressure, resulting in a more progressive and effective cough.

Monitoring is advantageously carried out by a computer processor coupled to sensors 306 (FIG. 18) configured to detect electrical or other signals generated by the patient. The computer processor analyzes the signals and implements the stimuli in accordance with the disclosure, to improve the timing and efficacy of the cough and swallowing responses, thereby protecting the airway to the therapeutic benefit of the patient.

Figure 15:
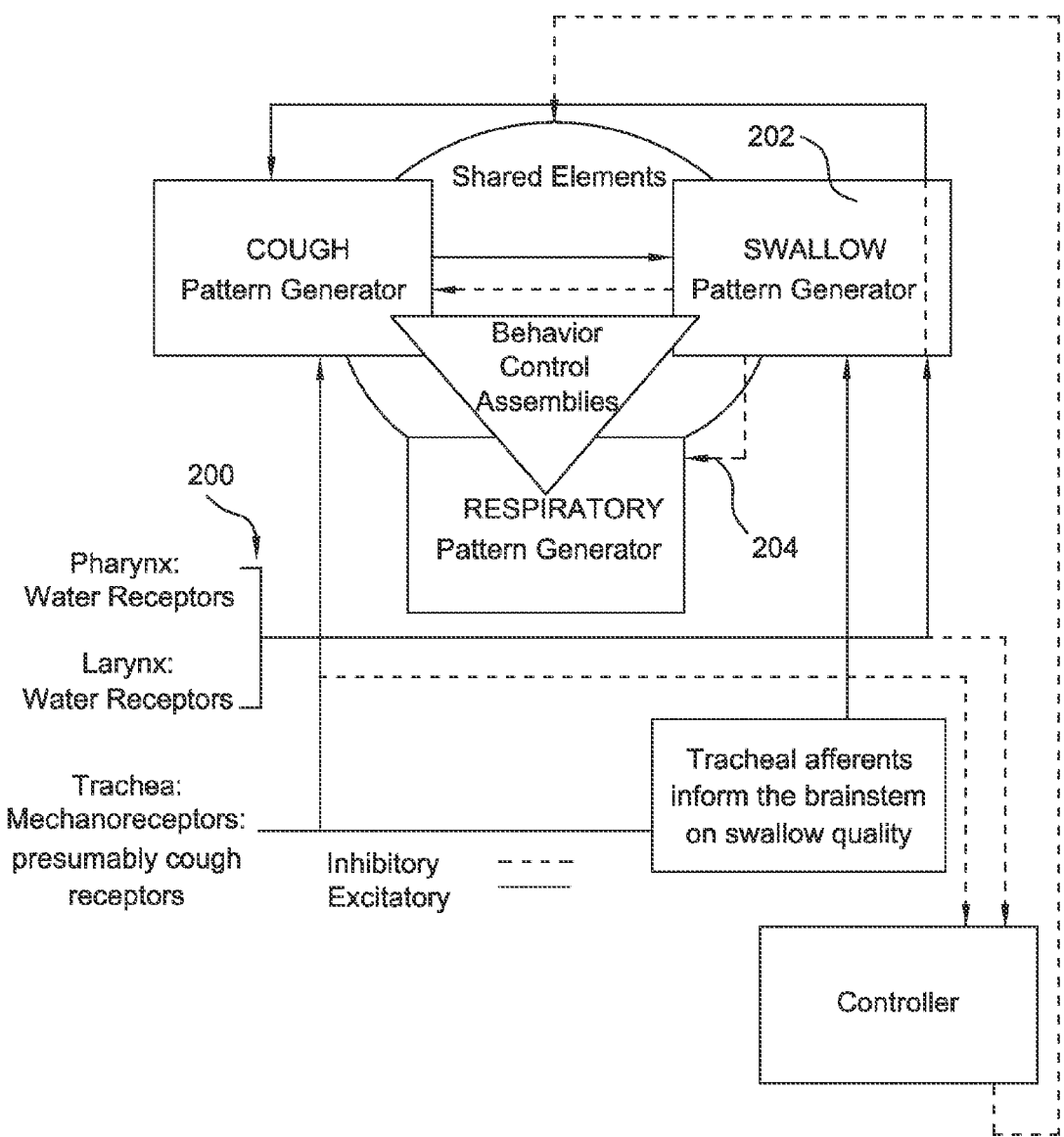
FIG. 15 illustrates inhibitory and excitatory pathways in the patient, and behavior controls, within the patient, including a controller of the disclosure.

In FIG. 15, it may be seen that a model used by the disclosure, as described in the context of FIG. 7, may be combined with a controller, for example a computer having a computer processor 802 (FIGS. 16-18), to form a closed-loop electrical stimulation control strategy to regulate the expression of coughing and swallowing, as described herein. The controller receives inputs from receptors in the pharynx and the larynx, for example as monitored by EMG, and the controller stimulates coughing, swallowing, and respiration using an imposition of electrical signals. The controller then measures the effect of these actions, and adjusts subsequent actions accordingly, to arrive at well timed and effective airway protection, including for example sealing of the trachea, coughing to remove contaminants within the airway, and swallowing to remove the contaminants from the pharynx. The device may further synchronize with respiratory patterns of the patient in real time, through EMG.

Stimulus parameters of devices of the disclosure shape motor responses to improve impairment of the execution of swallow and cough. Devices of the disclosure may be optimized for either clinical or home based use. For example, clinical devices may be constructed with more rugged or durable materials to withstand greater use, or may enable a wider array of configuration parameters, with respect to home based devices. In either configuration, devices assist a patient with protecting their airway, including assisting a patient with any of swallowing, weaning from mechanical ventilation, and coughing.

In one embodiment devices include wearable micro-chip controlled multi-modal system including a stimulation array that is self-controlled, or may be wired or wirelessly controlled or in communication with other electronic devices. For example, devices of the disclosure may be controlled through a mobile or web based application on a cell phone or other computing device. It is estimated that approximately 15 million people in the United States have symptoms of dysphagia and dystussia (disorder of cough). Accordingly, devices of the disclosure are adjustable for a wide variety of patient physiology, including a broad range of sizing support and electrical power output.

In an embodiment, the device of the disclosure provides a multi-modal stimulation array that is optimized to the patient's physiology based upon real time behavioral feedback from EMG, advantageously surface EMG, but intramuscular EMG may also be used. Advantageously, devices of the disclosure are light weight and or small in size, so that they may be wearable unobtrusive. It is further advantageous if they may be programmed through a wired or wireless connection to a computer or other electronic controller, so that the devices may remotely optimized to changes in a patient's condition. Optimization may thus be accomplished using an onboard controller of the device, or exclusively with a remotely connected controller, or by a combination of the two, to increase airway protection and reduce aspiration-related conditions. Wireless protocols include, for example, WiFi, Bluetooth, 4G, or any other wireless technology known or hereinafter developed.

Devices of the disclosure are advantageously positioned used in combination with other forms of therapeutic treatment, including swallowing and coughing exercises either during or in between uses of the device.

Figure 16:
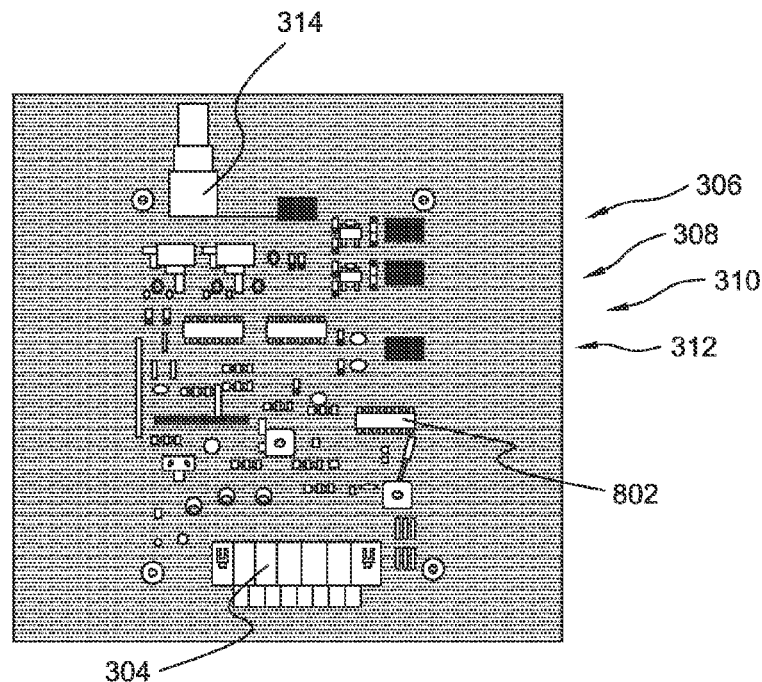
FIG. 16 depicts a control board of the disclosure.
Figure 17:
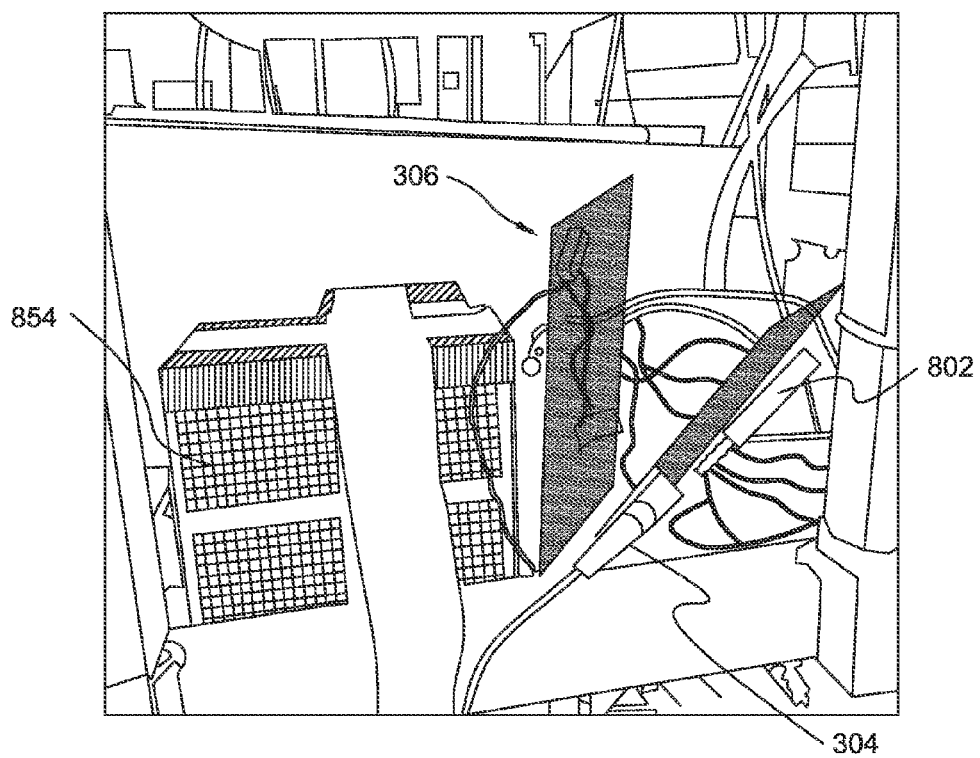
FIG. 17 depicts a signal generator and electronic boards forming a device of the disclosure.

Device 300 may include some or all of the components shown in FIGS. 16-18, which is a block diagram of an electronic device and associated components. In this example, an electronic device 300 is advantageously, but not necessarily, a wireless two-way communication device with data communication capabilities, and optionally voice communication capabilities, useful for example in the event of a breathing emergency. Such electronic devices communicate with a wireless voice or data network 850 using a suitable wireless communications protocol. Wireless voice communications are performed using either an analog or digital wireless communication channel. Data communications allow the electronic device 300 to communicate with other computer systems via the Internet. Examples of electronic devices that are able to incorporate the above described systems and methods include, for example, a data messaging device, a two-way pager, a cellular telephone with data messaging capabilities, a wireless Internet appliance or a data communication device that may or may not include telephony capabilities.

The illustrated electronic device 300 is an example electronic device that includes two-way wireless communications functions. Such electronic devices incorporate communication subsystem elements such as a wireless transmitter 810, a wireless receiver 812, and associated components such as one or more antenna elements 814 and 816. A digital signal processor (DSP) 808 performs processing to extract data from received wireless signals and to generate signals to be transmitted. The particular design of the communication subsystem is dependent upon the communication network and associated wireless communications protocols with which the device is intended to operate.

The electronic device 300 includes a microprocessor 802 that controls the overall operation of the electronic device 300. The microprocessor 802 interacts with the above described communications subsystem elements and also interacts with other device subsystems such as flash memory 806, random access memory (RAM) 804, auxiliary input/output (I/O) device 838, data port 828, display 834, keyboard 836, speaker 832, microphone 830, a short-range communications subsystem 820, a power subsystem 822, and any other device subsystems.

Device 300 further advantageously includes some or all of a frequency generator 308 capable of outputting the therapeutic varying frequency and voltage described herein. Additionally, sensors 306, advantageously including EMG and pressure sensing are provided. The foregoing elements 306 and 308 are advantageously in communication with and or under the control of processor 802, although they may be provided with their own logic and control, or they may be under the control of an external processor or logic circuit. In one embodiment, one or more aspects of elements 306 or 308 may be controlled by a manual adjuster, for example a potentiometer 314 (FIG. 16). Cables 304 or wireless signals connect subunits 306 and 308 to processor 802 or to one or more other logic or control units. Portions of device 300, including subunits 306 and 308 may be provided on one or more separate electronic circuit boards.

A battery 824 is connected to a power subsystem 822 to provide power to the circuits of the electronic device 300. The power subsystem 822 includes power distribution circuitry for providing power to the electronic device 300 and also contains battery charging circuitry to manage recharging the battery 824. The power subsystem 822 includes a battery monitoring circuit that is operable to provide a status of one or more battery status indicators, such as remaining capacity, temperature, voltage, electrical current consumption, and the like, to various components of the electronic device 300.

The data port 828 of one example is a receptacle connector 104 or a connector that to which an electrical and optical data communications circuit connector 800 engages and mates, as described above. The data port 828 is able to support data communications between the electronic device 300 and other devices through various modes of data communications, such as high speed data transfers over an optical communications circuits or over electrical data communications circuits such as a USB connection incorporated into the data port 828 of some examples. Data port 828 is able to support communications with, for example, an external computer or other device.

Data communication through data port 828 enables a user to set preferences through the external device or through a software application and extends the capabilities of the device by enabling information or software exchange through direct connections between the electronic device 300 and external data sources rather than via a wireless data communication network. In addition to data communication, the data port 828 provides power to the power subsystem 822 to charge the battery 824 or to supply power to the electronic circuits, such as microprocessor 802, of the electronic device 300.

Operating system software used by the microprocessor 802 is stored in flash memory 806. Further examples are able to use a battery backed-up RAM or other non-volatile storage data elements to store operating systems, other executable programs, or both. The operating system software, device application software, or parts thereof, are able to be temporarily loaded into volatile data storage such as RAM 804. Data received via wireless communication signals or through wired communications are also able to be stored to RAM 804.

The microprocessor 802, in addition to its operating system functions, is able to execute software applications on the electronic device 300. A predetermined set of applications that control basic device operations, including at least data and voice communication applications, is able to be installed on the electronic device 300 during manufacture. Examples of applications that are able to be loaded onto the device may be a personal information manager (PIM) application having the ability to organize and manage data items relating to the device user, such as, but not limited to, e-mail messages; text messaging; programming therapeutic events; reminding of maintenance tasks; notification of battery charge; setting or revising therapies, including changing frequency patterns, voltage patters, and the timing of therapeutic events; and the transmittal of information to care givers, nurses, or doctors.

Further applications may also be loaded onto the electronic device 300 through, for example, the wireless network 850, an auxiliary I/O device 838, Data port 828, short-range communications subsystem 820, or any combination of these interfaces. Such applications are then able to be installed by a user in the RAM 804 or a non-volatile store for execution by the microprocessor 802.

In a data communication mode, a received signal such as a text message or web page download is processed by the communication subsystem, including wireless receiver 812 and wireless transmitter 810, and communicated data is provided the microprocessor 802, which is able to further process the received data for output to the display 834, or alternatively, to an auxiliary I/O device 838 or the Data port 828. A user of the electronic device 300 may also compose data items, such as e-mail messages, using the keyboard 836, which is able to include a complete alphanumeric keyboard or a telephone-type keypad, in conjunction with the display 834 and possibly an auxiliary I/O device 838. Such composed items are then able to be transmitted over a communication network through the communication subsystem.

For voice communications, overall operation of the electronic device 300 is substantially similar, except that received signals are generally provided to a speaker 832 and signals for transmission are generally produced by a microphone 830. Alternative voice or audio I/O subsystems, such as a voice message recording subsystem, may also be implemented on the electronic device 300. Although voice or audio signal output is generally accomplished primarily through the speaker 832, the display 834 may also be used to provide an indication of the identity of a calling party, the duration of a voice call, or other voice call related information, for example.

Depending on conditions or statuses of the electronic device 300, one or more particular functions associated with a subsystem circuit may be disabled, or an entire subsystem circuit may be disabled. For example, if the battery temperature is low, then voice functions may be disabled, but data communications, such as e-mail, may still be enabled over the communication subsystem.

A short-range communications subsystem 820 provides for data communication between the electronic device 300 and different systems or devices, which need not necessarily be similar devices. For example, the short-range communications subsystem 820 includes an infrared device and associated circuits and components or a Radio Frequency based communication module such as one supporting Bluetooth® communications, to provide for communication with similarly-enabled systems and devices, including the data file transfer communications described above.

A media reader 860 is able to be connected to an auxiliary I/O device 838 to allow, for example, loading computer readable program code of a computer program product into the electronic device 300 for storage into flash memory 806. One example of a media reader 860 is an optical drive such as a CD/DVD drive, which may be used to store data to and read data from a computer readable medium or storage product such as computer readable storage media 862. Examples of suitable computer readable storage media include optical storage media such as a CD or DVD, magnetic media, or any other suitable data storage device. Media reader 860 is alternatively able to be connected to the electronic device through the Data port 828 or computer readable program code is alternatively able to be provided to the electronic device 300 through the wireless network 850.

All references cited herein are expressly incorporated by reference in their entirety. It will be appreciated by persons skilled in the art that the present invention is not limited to what has been particularly shown and described herein above. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

REFERENCES

Cabre, M., Serra-Prat, M., Palomera, E., Almirall, J., Pallares, R., & Clave, P. (2010). Prevalence and prognostic implications of dysphagia in elderly patients with pneumonia. *Age and ageing*, 39(1), 39.

Jones, U., Enright, S., & Busse, M. (2011). Management of respiratory problems in people with neurodegenerative conditions: a narrative review. *Physiotherapy*.

Pitts, T., Troche, M. S., Camaby-Mann, G., Rosenbek, J. C., Okun, M. S., & Sapienza, C M. (2010). Utilizing voluntary cough to detect penetration and aspiration during oropharyngeal swallowing in Parkinson's disease. *Chest*.

Smith Hammond, C. A., Goldstein, L. B., Homer, R. D., Ying, J., Gray, L., Gonzalez-Rothi, L., & Bolser, D. C. (2009). Predicting aspiration in patients with ischemic stroke: comparison of clinical signs and aerodynamic measures of voluntary cough. *Chest*, 135(3), 769-777. doi: chest.08-1122 [pii] 10.1378/chest.08-1122

Smith Hammond, C. A., Goldstein, L. B., Zajac, D. J., Gray, L., Davenport, P. W., & Bolser, D. C. (2001). Assessment of aspiration risk in stroke patients with quantification of voluntary cough. *Neurology*, 56(4), 502-506.

Sue Eisenstadt, E. (2010). Dysphagia and aspiration pneumonia in older adults. Journal of the American academy of Nurse Practitioners, 22(1), 17-22.

Van Den Eeden, S. K., et al., *Incidence of Parkinson's disease: variation by age, gender, and race/ethnicity*. American Journal of Epidemiology, 2003. 157(11): p. 1015-1022.

Brookmeyer, R., S. Gray, and C. Kawas, *Projections of Alzheimer's disease in the United States and the public health impact of delaying disease onset*. American Journal of Public Health, 1998. 88(9): p. 1337.

Fernandez, H. and K. Lapane, *Predictors of mortality among nursing home residents with a diagnosis of Parkinson's disease*. Medical science monitor: international medical journal of experimental and clinical research, 2002. 8(4).

Ertekin, C. and J. B. Palmer, *Physiology and electromyography of swallowing and its disorders*. Suppl Clin Neurophysiol, 2000. 53: p. 148-54.

Jean, A., *Brain stem control of swallowing: neuronal network and cellular mechanisms*. Physiological Review, 2001. 81(2): p. 929-69.

Canning, B. J., *Anatomy and neurophysiology of the cough reflex*. Chest, 2006. 129(1 suppl): p. 33S.

Fontana, G. A. and F. Lavorini, *Cough motor mechanisms*. Respir Physiol Neurobiol, 2006. 152(3): p. 266-81.

Lavietes, M. H., et al., *Airway dynamics, oesophageal pressure and cough*. Eur Respir J, 1998. 11(1): p. 156-61.

Oku, Y., I. Tanaka, and K. Ezure, *Activity of bulbar respiratory neurons during fictive coughing and swallowing in the decerebrate cat*. The Journal of Physiology, 1994. 480(Pt 2): p. 309.

Satoh, I., et al., *Upper airway motor outputs during sneezing and coughing in decerebrate cats*. Neuroscience research, 1998. 32(2): p. 131-135.

Gestreau, C., et al., *Activity of dorsal respiratory group inspiratory neurons during laryngeal-induced fictive coughing and swallowing in decerebrate cats*. Experimental brain research, 1996. 108(2): p. 247-256.

Lalmohamed A, et al., *Causes of death in patients with multiple sclerosis and matched referent subjects: a population-based cohort study*. Eur J. Neurol., 2012.

Lechtzin N., *Respiratory effects of amyotrophic lateral sclerosis: problems and solutions*. Respir Care, 2006. 51(8) 871-81.

REFERENCE LIST 104 receptacle connector
300 device
304 cables or wireless connection
306 sensors/EMG sensing
308 frequency generator/power supply
802 processor(s)
804 RAM
806 flash memory
808 DSP
810 wireless transmitter
812 wireless receiver
814 antenna(s)
816 antenna(s)
820 short-range comm. system
822 power subsystem
824 battery
828 data port
830 microphone
832 speaker
834 display
836 keyboard
838 I/O device
850 data network
860 media reader

What is claimed is:

1. A method of protecting an airway of a patient, comprising:
   monitoring muscles of the patient to detect an attempted cough or swallow;
   applying an electrical stimulus to afferent nerves of at least one of the neck and head of the patient, in a pattern of varying non-zero values of at least one of pulse width, amplitude or frequency over time, the applied electrical stimulus operative to promote an efficacious cough or swallow.

2. The method of claim 1, the electrical stimulus including a voltage within a range of greater than zero volts and less than 20 volts.

3. The method of claim 1, wherein the electrical stimulus is swept through a range of between at least about 4 Hz to not more than about 30 Hz.

4. The method of claim 1, an electrical stimulus is applied before the patient has attempted to swallow, and an electrical stimulus is applied between about 1 millisecond to about 0.5 seconds after the patient has attempted to swallow or has swallowed.

5. The method of claim 1, wherein monitoring muscles is performed using EMG.

6. The method of claim 5, wherein the electrical stimulus is applied after the incidence of predetermined markers in the EMG signal.

7. The method of claim 6, wherein sensed EMG information is analyzed by one or more computer processors, the processors operative to initiate the application of the electrical stimulus.

8. The method of claim 1, wherein monitoring of muscles of the patient is carried out by an electronic device.

9. The method of claim 8, wherein the patient may indicate to the electronic device that a swallow or cough is impending.

10. A device for protecting an airway of a patient, comprising:
- a plurality of electrodes positionable upon skin of the patient, the electrodes configured for capturing electromyographic information and for transmitting a stimulating electrical signal to the body;
- a signal generator configured to generate a signal in a pattern of varying non-zero values of at least one of pulse width, amplitude, or frequency across at least two of the plurality of electrodes, the signal generated configured to stimulate efferent nerves of at least one of the neck and head of the patient; and
- software stored on non-transitory media, executable by at least one processor, the software configured to analyze the electromyographic information to identify an attempted cough or swallow, the processor configured to cause the at least two electrodes to apply an electrical stimulus, generated from the signal generator, to the afferent nerves if the analysis indicates an attempted cough or swallow.

11. The device of claim 10, the adjusting including sweeping the signal over a range of values over time to promote an efficacious cough or swallow.

12. A method of protecting an airway of a patient, comprising:
- monitoring muscles of the patient to detect an attempted cough or swallow using sensed EMG information;
- analyzing information pertaining to monitoring muscles by at least one computer processor to identify an attempted cough or swallow; and
- applying an electrical stimulus to at least one of the neck and head of the patient if the analysis indicates an attempted cough or swallow, the signal configured to stimulate an efferent nerve of at least one of the neck and head, and varying non-zero values of at least one of an amplitude or frequency over time, the applied electrical stimulus thereby operative to promote an efficacious cough or swallow.

13. The method of claim 12, the electrical stimulus including a voltage within a range of greater than zero volts and less than 20 volts.

14. The method of claim 12, wherein the frequency is swept through a range, the range within at least about 4 Hz to not more than about 30 Hz.

15. The method of claim 12, wherein the electrical stimulus is applied before the patient has attempted to swallow, and an electrical stimulus is applied between about 1 millisecond to about 0.5 seconds after the patient has attempted to swallow or has swallowed.

16. The method of claim 12, wherein the electrical stimulus is applied after the incidence of predetermined markers in the EMG signal.

17. The method of claim 12, wherein sensed EMG information is analyzed by one or more computer processors, the processors operative to initiate the application of the electrical stimulus.

18. The method of claim 12, wherein monitoring of muscles of the patient is carried out by an electronic device.

19. The method of claim 18, wherein the patient may indicate to the electronic device that a swallow or cough is impending.

20. The method of claim 12, wherein varying non-zero values includes changing the stimulation for a patient to decrease a possibility of habituation to the stimulus by the patient.

21. The method of claim 12, wherein the signal is applied for periods longer than 20 seconds, to bring about synaptic plasticity within the patient.

* * * * *